United States Patent [19]

Wiesenthal et al.

[11] Patent Number: 4,727,864

[45] Date of Patent: Mar. 1, 1988

[54] PROTECTIVE SLEEVE FOR THE LEAK-PROOF COVERAGE OF BODY PARTS

[75] Inventors: Peter Wiesenthal; Beatus Ille, both of Winsen, Fed. Rep. of Germany

[73] Assignees: Ille GmbH, Fed. Rep. of Germany; Chemie Lenz AG, Austria

[21] Appl. No.: 803,546

[22] Filed: Dec. 2, 1985

[30] Foreign Application Priority Data

Dec. 7, 1984 [DE] Fed. Rep. of Germany ....... 3444626

[51] Int. Cl.$^4$ .............................................. A61F 13/00
[52] U.S. Cl. ..................................................... 128/82
[58] Field of Search ............. 128/87 R, DIG. 20, 157, 128/82, 83, 165

[56] References Cited

U.S. PATENT DOCUMENTS

| | | | |
|---|---|---|---|
| 2,244,871 | 6/1941 | Guinzburg | 128/157 |
| 3,741,203 | 6/1973 | Liman | 128/82 |
| 4,187,851 | 2/1980 | Hauser | 128/157 X |
| 4,224,935 | 9/1980 | Metelnick | 128/165 X |
| 4,523,586 | 6/1985 | Couri | 128/82 |

*Primary Examiner*—Richard T. Stouffer
*Attorney, Agent, or Firm*—McGlew and Tuttle

[57] ABSTRACT

A protective sleeve, particularly for human arms and legs, uses a sack-like synthetic material film with a slip-in opening. A preferably adhesive, band-shaped sealing strip is fastened at the rim of the slip-in opening over a part of its circumference and projects over the rim of the film. The strip forms a freely projecting member of such length and such surface that the ends of the sealing strip, after enclosing a body part to be covered, overlap, one adhering on the other.

3 Claims, 3 Drawing Figures

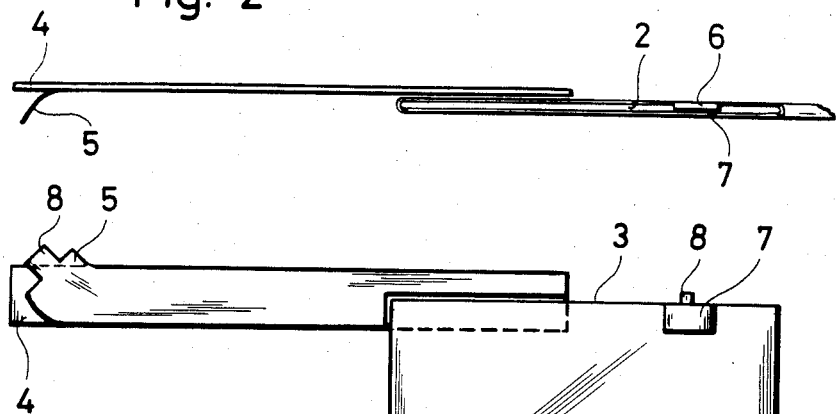
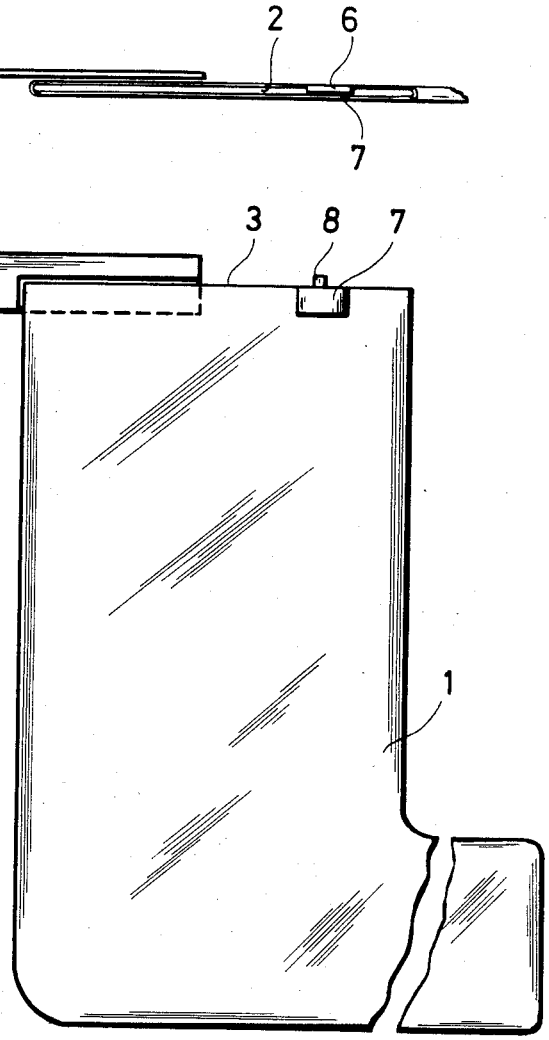
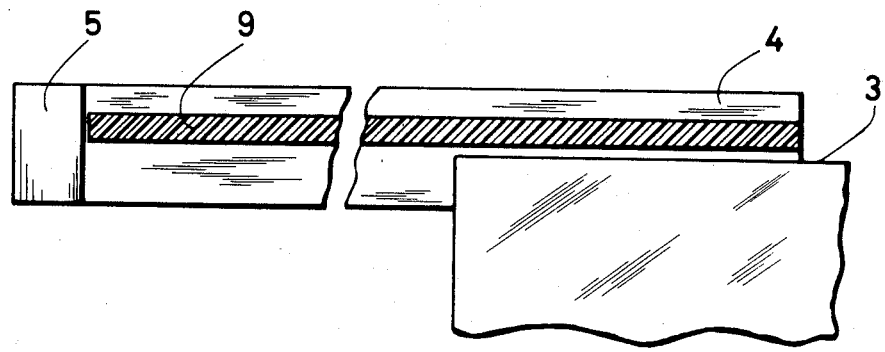

PROTECTIVE SLEEVE FOR THE LEAK-PROOF COVERAGE OF BODY PARTS

FIELD AND BACKGROUND OF THE INVENTION

The present invention relates in general to medical bandages and casts, and in particular to a new and useful protective sleeve which is meant for engagement around a bandage or cast to provide a leakproof covering therefor.

When body parts, for example human arms or legs, are covered by bandages or casts, and in particular when these bandages or casts, such as for example plaster casts, cannot be taken off over a long period of time, there is a pressing need to cover these bandages or casts against the ingress of water, for example during showering. In many cases, patients have helped themselves by slipping sack-like synthetic material sleeves over the body parts and then fastened them at the body part, for example with the aid of strings, rubber rings or bands. Of course, such covers do not result in a water-tight closure, because the synthetic material films are folded together in every case and form fine channels through which water can penetrate, for example during showering.

If one takes a normal synthetic material fiber and utilizes an adhesive strip, such having become known under the designation HANSAPLAST, for the sealing of the film at the body part, then a relatively good sealing against the ingress of water is attained. The application of such a protective film or sleeve is however extraordinarily difficult, at least at the arms, because the protective sleeve must be held fast and the adhesive strip must be applied at the same time. This kind of adhesive strip is not intended for sealing and is therefore not water-tight. It adheres poorly to moist body places and is at individual body parts to be removed again only with discomfort, because the adhesive force is great.

SUMMARY OF THE INVENTION

The invention is based on the task of creating a protective sleeve which is specially suitable for the covering of body parts and in that sleeve makes use of a sack-like synthetic material film or foil, e.g. of polyethylene, with a slip-in opening. The protective sleeve should be easy to fasten and become liquid-tight, even using only one hand, and result in a good closure with coarse adaptation to the outlines of the body parts to be covered, for example a foot.

According to the invention, this is attained by using a preferably adhesive, band-shaped sealing strip which is fastened at the rim of the slip-in opening over a part of its circumference, and projects over the rim of the film against the direction of insertion for the body part, and forms a freely projecting strip of such length and such surface that the ends of the sealing strip, after enclosing of the body part to be covered, overlap, one adhering on the other.

It is particularly advantageous to make the sealing strip of toughly elastic material, and particularly of a material which is friendly to the skin. The strip is liquid-tight and adheres well, possibly also on moist body parts, but not too firmly. For the enclosing of a body part by the inventive sealing strip, the adhesion strength at the body itself is also not so important as the tight closure and the good adhesion in the region of overlapping. For holding the sleeve fast, for example during single-handed operation, it is advantageous to fasten a piece of adhesive strip at the inside of the sleeve as an adhesion place or area which, just as the sealing strip in the region of applied adhesive layers, is covered by a protective film which is pulled off shortly before use. Through this adhesive strip which is applied on the inside of the sleeve at the adhesion area, the protective sleeve is fixed at the body part so that the sealing strip can then be laid tautly around the body part with the inclusion of an upper edge of the protective sleeve.

In special cases, the upper edge or rim of the protective sleeve can additionally be provided with a softly elastic bead which for example consists of sponge rubber and is applied on the inside and at the sealing strip, closely above the rim of the protective sleeve. Thereby, a liquid sealing could also be attained by a sealing strip which adheres on the body parts themselves only very little or not at all, and adheres one on the other only in the overlapping region.

Accordingly an object of the present invention is to provide a protective cover for the leakproof coverage of a body part, comprising a synthetic material sleeve having at least one slip-in opening with a rim for receiving the body part in a slip-in direction, an adhesive band-shaped sealing strip having opposite ends and fastened to said rim over a portion of the circumference of said rim, said strip projecting over said rim in a direction opposite to said slip-in direction and extending laterally of said rim by a length which is sufficient so that the opposite ends of said strip overlap when said strip is engaged around the body part. A further object of the invention is to provide such a protective cover which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the drawings:

FIG. 1 is a side elevational view of the protective sleeve or covering, in accordance with the invention;

FIG. 2 is a top plan view of the protective sleeve or covering shown in FIG. 1; and FIG. 3 is a fragmentary side elevational view, on an enlarged scale, of a sealing band and a top portion of the protective sleeve in accordance with the invention.

DESCRIPTION OF THE PREFERRED EMBODIMENT

FIG. 1 (in side elevation) and FIG. 2 (in plan view) show a protective sleeve 1, for example in the outline shape of a lower leg and foot, which is constructed to be sack-like and provided with a slip-in opening 2. A sealing strip 4 is rigidly fastened at the upper rim or edge 3 of the sleeve 1 and covered by a protective film or cover layer 5. Furthermore, a further piece of adhesive strip 6 is fastened in the region of the upper rim and covered by a protective or cover layer film 7. Both protective films 5 and 7 have tags 8, with the aid of which the films can be pulled off. The films 5 and 7 may also have cut or incision lines of known type, which aid in the removal of the films.

The FIG. 3 shows a detail of the adhesive strip 4, on which a bead 9 of a softly elastic material, for example sponge rubber is applied in a thickness of, for example, 1 to 5 millimeters above the rim 3 of the sleeve 1. This bead 9 creates a tight closure even when the sealing strip 4 itself does not adhere to the body part (in this case, the leg).

The length of the freely projecting strip and the associated protective film 5 is so dimensioned that the body part to be protected is encircled and the ends of the adhesive strip overlap after the tight enclosing of the body part, so that they hold each other adhesively.

Should the protective sleeve or cover 1 be meant for use over long periods of time, and for example may be exposed to rain and the like, the protective covering is advantageously made of semi-permeable (breathable) material. Such material is known to be impervious to water while permitting vapors and air to pass therethrough. This avoids condensation and moisture due to sweating inside the protective covering.

The material of covering or sleeve 1 may be polyethylene. The adhesive strip 4 can be made of the same material and is provided with a layer of adhesive. This layer of adhesive is provided on the surface of strip 4 which is visible in FIG. 3. FIG. 3 also shows a remnant of protective film 5. The remainder of film 5 was peeled away from the adhesive layer of strip 4. In the same fashion the protective film 7 on the adhesive layer 6 in FIG. 1, can also be peeled away to expose the adhesive layer 6.

While a specific embodiment of the invention has been shown and described in detail to illustrate the application of the principles of the invention, it will be understood that the invention may be embodied otherwise without departing from such principles.

What is claimed is:

1. A protective cover for the leakproof coverage of a body part, comprising a sock-shaped sleeve made of thin-walled foldable plastic foil and having a top opening defining a slip-in entrance extended into said sleeve and a rim surrounding the opening, an elastic band-shaped sealing strip of elastic material having an adhesive surface along its length and one end portion which is adhesively secured to the outside of said sleeve adjacent the rim and extending beyond said rim and extending around at least a part of the circumference of said sleeve, said sealing strip projecting beyond said rim on one side of said sleeve and extending by a length sufficient so that it may encompass the complete rim and overlap the opposite end of said sealing strip and be adhered thereto and to the body part when said strip is engaged around the body part, and including a spot adhesive surface means adhered to a minor portion of the inside of said sleeve close to said entrance for adhesion of said sleeve to the body part, said spot adhesive surface means for adhesion of said sleeve directly to the body part prior to the closure of the opening of said sleeve, said sleeve being closed by the adhering of said sealing strip around said opening, so as to allow said sleeve to be retained relative to the body part by said spot adhesive means prior to the adhering of said sealing strip as said sealing strip encompasses the complete rim of the opening.

2. A protective cover according to claim 1 including a protective film covering the adhesive surface of said sealing strip which is removable.

3. A protective cover according to claim 2 wherein said protective film includes a gripping tab extending beyond said adhesive surface.

* * * * *